US00PP16740P3

(12) United States Plant Patent
Beineke

(10) Patent No.: US PP16,740 P3
(45) Date of Patent: Jun. 27, 2006

(54) BLACK CHERRY TREE NAMED 'AFTC-1'

(50) Latin Name: *Prunus serotina Ehrh*
Varietal Denomination: AFTC-1

(75) Inventor: Walter F. Beineke, West LaFayette, IN (US)

(73) Assignee: American Forestry Technologies, Inc., West Point, IN (US)

( * ) Notice: Subject to any disclaimer, the term of this patent is extended or adjusted under 35 U.S.C. 154(b) by 52 days.

(21) Appl. No.: 10/976,676

(22) Filed: Oct. 29, 2004

(65) Prior Publication Data

US 2006/0095994 P1 May 4, 2006

(51) Int. Cl.
*A01H 5/00* (2006.01)

(52) U.S. Cl. ..... Plt./181
(58) Field of Classification Search ..... Plt./182, Plt./181
See application file for complete search history.

(56) References Cited

U.S. PATENT DOCUMENTS

PP8,721 P 5/1994 Calder
PP11,108 P 10/1999 Andersen et al.

OTHER PUBLICATIONS

Downey, Suzanne L., Lezzoni, Amy F. (2000) Polymorphic DNA Markers in Black Cherry (*Prunus serotina* ) Are identified Using Sequences from Sweet Cherry, Peach and Sour Cherry. J. Amer. Soc. Hort. Sci. 125(1); 76–80.

*Primary Examiner*—Kent Bell
*Assistant Examiner*—June Hwu
(74) *Attorney, Agent, or Firm*—Alice O. Martin; Barnes & Thornburg LLP

(57) ABSTRACT

A new and distinct cultivar of black cherry tree (*Prunus serotina Ehrh*) which is distinctly characterized by extremely rapid growth rate, strong central stem tendency, excellent straightness, and insect and disease resistance, thereby producing excellent timber qualities, the trait of commercial interest. This new variety of black cherry tree was discovered by the applicant near West Lafayette, Tippecanoe County, Ind., in a black cherry planting. This selection has been designated as CH 5 in records maintained by the applicant on the performance of this selection and grafts made from the selection, and will be known hereafter as 'AFTC-1'.

4 Drawing Sheets

Latin name of the genus and species: *Prunus serotina Ehrh.*
Variety: 'AFTC-1'.

BACKGROUND OF THE INVENTION

This new variety of black cherry tree (*Prunus serotina Ehrh.*) was discovered by the applicant near West Lafayette, Tippecanoe County, Ind. in a 120 tree black cherry planting. This selection has been designated as CH5, in records maintained by the applicant on the performance of this selection, and grafts made from the selection, and will be known henceforth as 'AFTC-1'.

BRIEF SUMMARY OF THE INVENTION

Black cherry trees are sought for veneer and lumber. (Downey and Iezzoni, 2000).

A new and distinct cultivar of black cherry tree (*Prunus serotina Ehrh*) is distinctly characterized by extremely rapid growth rate, strong central stem tendency, and excellent straightness, thereby producing excellent timber qualities, the trait of commercial interest. 'AFTC-1' was 5 years old when described at a location near West Lafayette, Ind. The parentage of 'AFTC-1' is unknown. The seedlings in the planting were purchased from a commercial nursery. The planting is located in Shelby township at 440 N. 725 W. in section 24, R6W, T23N on Ceresco loam soil type, a well-drained highly fertile soil.

After the original clone was selected, and assigned an identity number of CH5 the aforesaid tree was reproduced by collecting scions from it and grafting these onto common black cherry rootstock at American Forestry Technologies, Inc., West Point, Ind. These asexual reproductions ran true to the originally discovered tree and to each other in all respects.

Color values used were from the Munsell Color Chart for Plant Tissues.

'AFTC-1' is hardy in USDA zones 4,5,6,7, and 8.

BRIEF DESCRIPTION OF THE DRAWINGS

FIG. 2 is a photograph showing the branch angle of 'AFTC-1'.

FIG. 3 is a photograph showing the leaves of 'AFTC-1'.

FIG. 4 is a photograph showing the flowers of 'AFTC-1'.

DETAILED BOTANICAL DESCRIPTION

Figure 1:
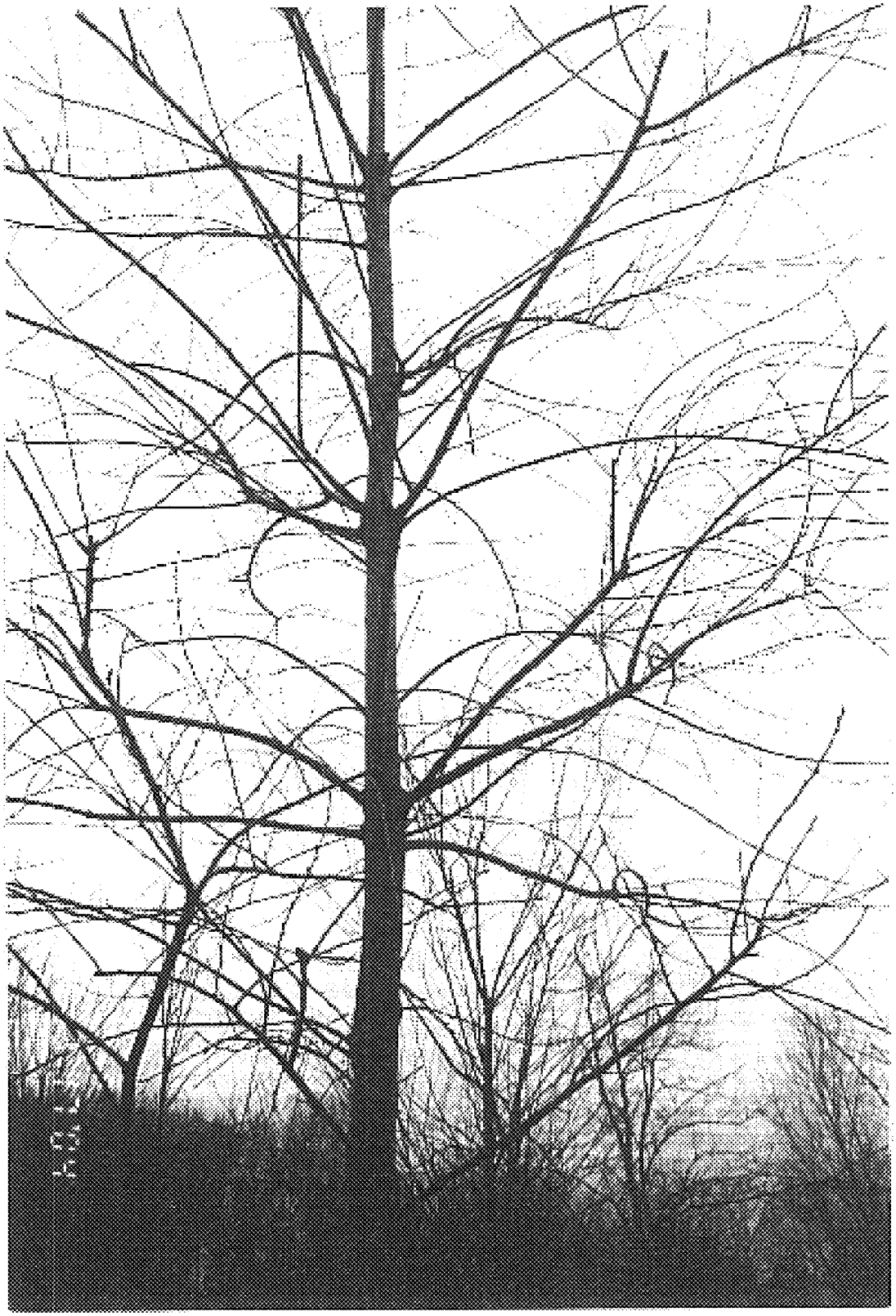
FIG. 1 is a photograph showing the timber form of 'AFTC-1'.

The botanical details of this new and distinct variety of cherry tree are as follows:

Tree:

*Size.*—32 ft. at 5 years; crown diameter of 8 ft. — very narrow.

*Vigor.*—Vigorous.

*Growth rate.*—Very rapid, 39.9% larger in diameter than the average (2.86 inches) of the plantation consisting of 120 black cherry trees planted the same year on the same land, Diameter at 4½ feet above the ground at 5 years was 4.0 inches, for an average growth rate of 0.80 inches per year.

*Form.*—Excellent timber form, 'AFTC-1' rates 1 on a 1 to 5 scale. Stem form was 59.3% better than the average (2.46) of the entire plantation. Stem form was obtained by subjectively rating the straightness of the main stem on a scale of 1 to 5 with 1 representing a prefectly straight stem; 2, slight crook or deviation of the central stem (no crooks); 3, about average straightness; 4, several severe crooks or a single fork; and 5, a very crooked, forked and/or leaning central stem.

Branches and trunk:

*Branch and trunk color.*—One year old branches, reddish brown — 7.5YR4/4 on the Munsell Color Chart for Plant Tissues; Older branches, reddish-brown — 7.5YR4/4 on the Munsell Color Chart for Plant Tissues; mature trunk and branches, mottled grays, browns — 7.5YR5/2, 7.5YR7/2 and 2.5Y6/2 on the Munsell Color Chart for Plant Tissues.

*Branch and trunk characteristics.*—One year old branches, slender, glabrous with gray bloom; older branches, smooth; mature trunk and branches, flaky, loose edges, typical of the species.

*Internode length.*—Average, upon visual inspection; 0.8 inches.

*Branch lenticels.*—Abundant, very elongated, light yellow-gray — 7.5YR8/2 on the Munsell Color Chart for Plant Tissues. The lenticels of 'AFTC-1' average 0.15" long and 0.03" wide. This compares to an average of 0.14" long and 0.05" wide for the 4 surrounding trees. On 1½ inch diameter branches 'AFTC-1' averages 19 lenticels per square inch of surface area. This compares to an average of 29 lenticels per square inch of surface area of the surrounding 4 trees. Therefore, while the size of the lenticels is about the same, 'AFTC-1' averages about 10 fewer lenticels per square inch than the surrounding trees.

*Branch angle.*—Average, 65°. Black cherry trees in this planting average 40°.

Leaves:

*Leaves.*—Size — Large; average length including petiole — 5.6"; average width 1.94"; lanceolate, acutely pointed, base — rounded, typical of species. Much larger than surrounding trees in the same planting which averaged 4.1 inches long and 1.4 inches wide. When compared to species descriptions, 'AFTC-1' is at the upper end of leaf size since leaf length varies from 2 to 6 inches and width from 1 to 2 inches wide. (Deam, 1953; Harlow et al., 1996; Leopold et al., 1998).

*Thickness.*—Thin.

*Texture.*—Upper surface, waxy, smooth, glabrous; Lower surface, glabrous, with tufts of brown pubescence at vein junctions.

*Margins.*—Serrated.

*Color.*—Upper Surface — green (7.5GY4/6 on the Munsell Color Chart for Plant Tissues); Lower surface — light green (7.5GY6/4 on the Munsell Color Chart for Plant Tissues).

*Petioles.*—Length — 0.84"; Color — yellow-green (2.5GY8/6 on the Munsell Color Chart for Plant Tissues). The surface of the petiole is smooth and waxy. Small glands are located at the base of the leaf petiole.

*Buds.*—Typical of species — pointed, usually 8 imbricate scales, glabrous, larger than average — 0.30"; Color — brownish red (7.5YR5/6 on the Munsell Color Chart for Plant Tissues).

Flowering habit:

*Flowers.*—Abundant — begin flowering at a very young age — 2 years. Greater than average number of flowers per raceme — 43.5. Average is about 38. Shorter than average raceme length of 4.6 inches. Average is about 5.5 inches. It is impossible to measure raceme diameter because flowers jut in and out and droop. Average flower size is 0.72 inches in diameter. Petal number is 5 on all trees. Petal color is pure white (not on Munsell Chart). The flowers of black cherry do not vary much from one tree to another. The flower has 1 pistil which averages 0.15 inches long and 16 stamens which average 0.32 inches long. Pistil color is light green-yellow — 2.5 GY 8/6 and stamen color is yellow — 5Y 8/10 .

*Flowering season.*—Mid May, earlier than average. Black cherry varies from mid-May to late June in the same region.

Fruiting habit:

*Size.*—Larger than average berry size — 0.35 inches in diameter. [Berry size in this planting averages 0.25 inches.] Shape is round. Surface — smooth, waxy. When compared to the species descriptions, 'AFTC-1' is about average overall since berry diameter varies from 0.25 to 50 inches. (Deam, 1953, Harlow et al., 1996; Leopold et al. 1998).

*Number.*—Fewer than average number of berries per raceme —about 10.6. [Black cherry averages 20 berries per raceme in this planting.]

*Ripening period.*—Much later than most black cherry — late August into early September. Black cherry trees ripen in late July to mid August in the same region.

*Color when ripe.*—Dark purple (5RP3/2 on the Munsell Color Chart for Plant Tissues).

Seed habit:

*Size.*—Larger than average —0.32 inches long. 0.27 inches in suture plane; 0.23 inches cheek to cheek. Black cherry averages 0.28 inches long, 0.25 inches in suture plane, and 0.21 inches cheek to cheek.

Insects and disease: A combination of insects and disease cause gum spots, a defect in the wood of black cherry trees. These insects and disease include lesser peach tree borer, cambial miner, and black knot fungus. On a scale of 1 to 5 with 1=no indication of insects or disease to 5=extreme susceptibility, 'AFTC-1' rates a 1 and shows absolutely no indication of susceptibility to any of these insects and disease. The plantation average is 2.1 for a 52.4% improvement of 'AFTC-1' over the other trees in the plantation.

Leaf spot of cherry is a disease that causes brown lesion on leaves and early defoliation. This is not a disease of consequence to the survival or growth of the tree. 'AFTC-1' is average in resistance (rating 3 on a 1–5 scale) while the plantation average is 3.3. A rating of 1 means the leaves have only a few leaf spots to 5 which indicates the leaves are covered with spots which causes considerable early defoliation.

DOCUMENTS CITED

Deam, C. C. Trees of Indiana (1954). p. 231.

Downey, Suzanne L., Iezzoni, Amy F. (2000) Polymorphic DNA Markers in Black Cherry (*Prunus serotina*) Are Identified Using Sequences from Sweet Cherry, Peach, and Sour Cherry. *J. Amer. Soc. Hort. Sci.* 125 (1); 76–80.

Harlow, Wm M., E. S. Harrar, J. W. Hardin and F. M. White (1996). Textbook of Dendrology 9 $^{th}$ Ed., p. 405.

Leopold, D. J., WmC. McComb and R. N. Muller (1998). Trees of the Central Hardwood Forests of North Amercia. p. 315.

I claim:

1. A new and distinct variety of black cherry tree named 'AFTC-1' substantially as illustrated and described, which has extremely rapid growth rate, strong central stem tendency, and excellent straightness, thereby producing excellent timber qualities.

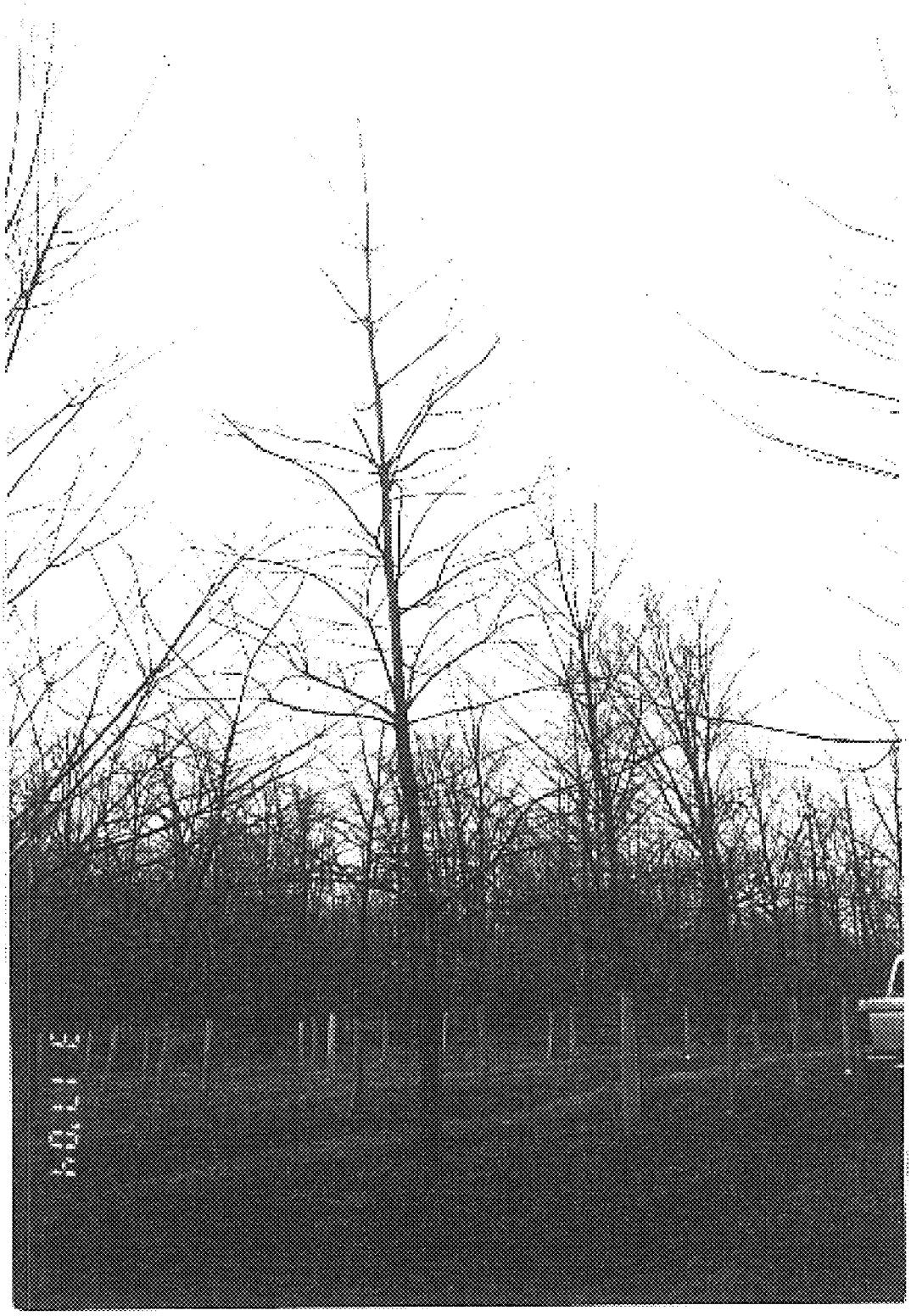

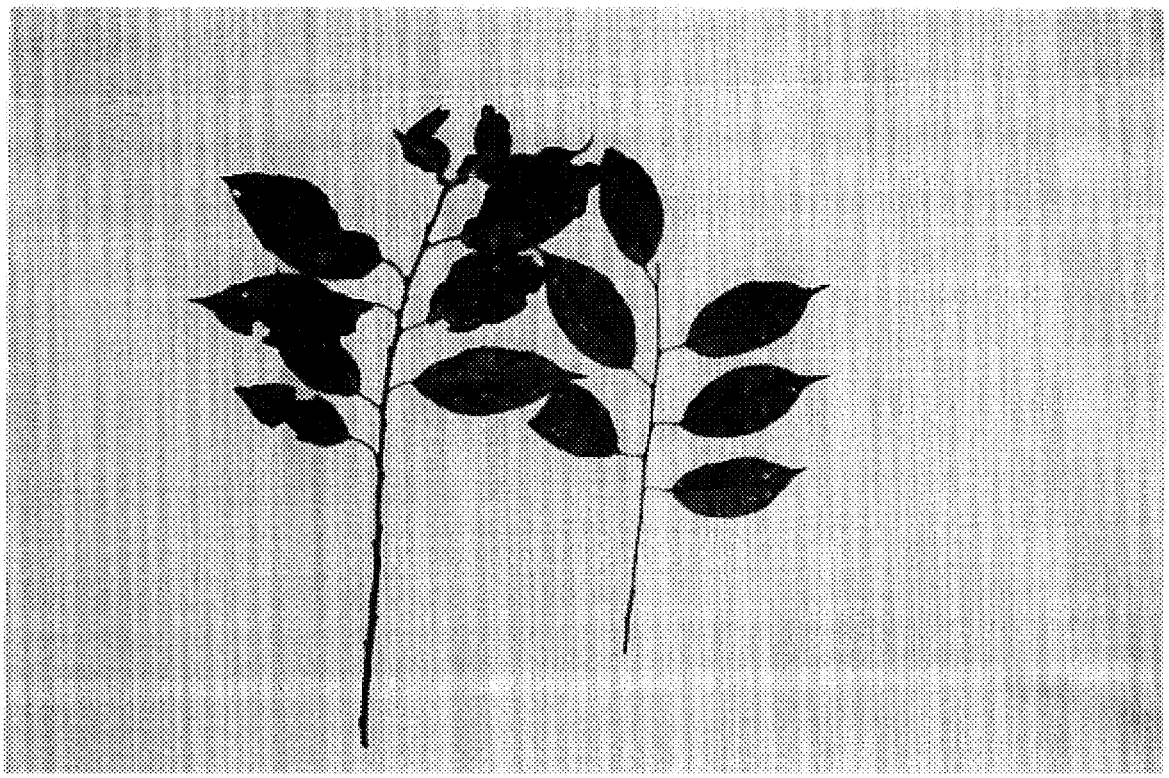

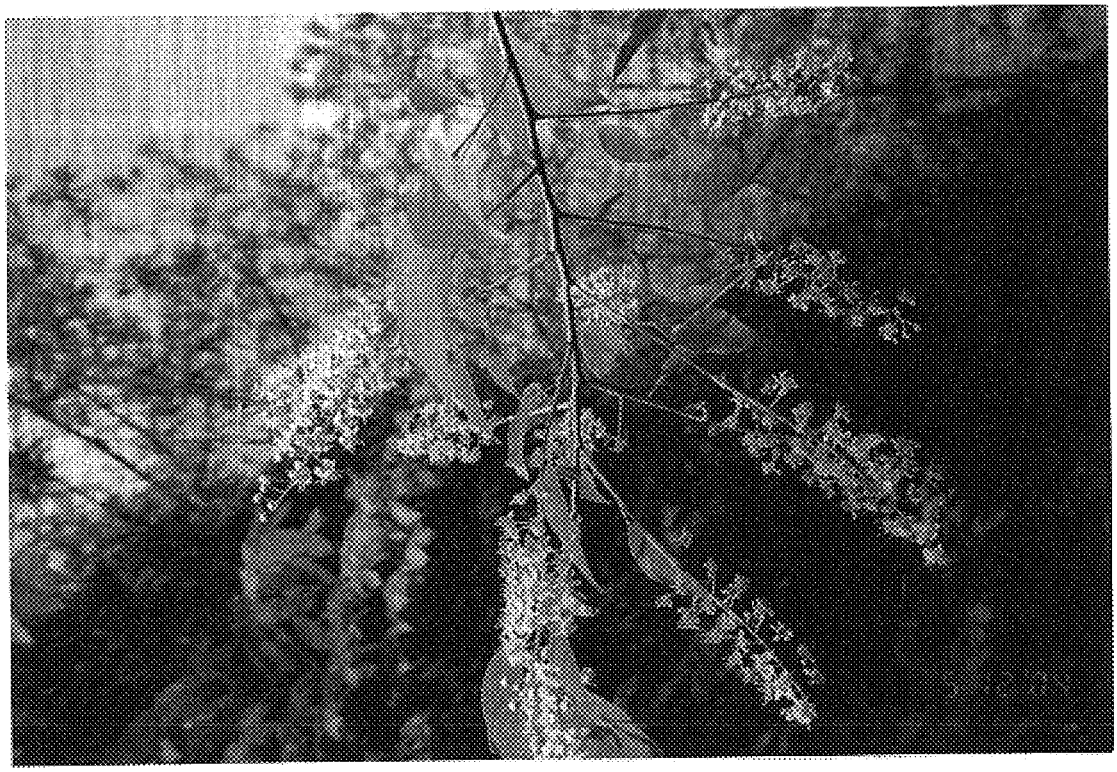

* * * * *